United States Patent [19]

Clark, Jr. et al.

[11] Patent Number: 4,855,677
[45] Date of Patent: Aug. 8, 1989

[54] MULTIPLE COIL EDDY CURRENT PROBE AND METHOD OF FLAW DETECTION

[75] Inventors: William G. Clark, Jr.; Michael J. Metala, both of Murrysville, Pa.

[73] Assignee: Westinghouse Electric Corp., Pittsburgh, Pa.

[21] Appl. No.: 167,289

[22] Filed: Mar. 11, 1988

[51] Int. Cl.$^4$ .................................... G01N 27/82
[52] U.S. Cl. .................................... 324/238; 324/232; 324/220; 324/262
[58] Field of Search .................. 324/219–221, 324/226–229, 232, 234, 237, 238, 239, 240, 242, 243, 262

[56] References Cited

U.S. PATENT DOCUMENTS

| | | | |
|---|---|---|---|
| 2,992,390 | 7/1961 | De Witte | 324/220 |
| 3,976,936 | 8/1976 | Nishino | 324/232 |
| 4,016,487 | 4/1977 | Neumaier | 324/232 |
| 4,088,953 | 5/1978 | Sarian | 324/232 |
| 4,234,848 | 11/1980 | Diem et al. | 324/262 |
| 4,325,026 | 4/1982 | Cooper, Jr. et al. | 324/232 |
| 4,355,281 | 10/1982 | Toth et al. | 324/232 |
| 4,467,281 | 8/1984 | Davis et al. | 324/232 |
| 4,529,936 | 7/1985 | Rebour | 324/238 |
| 4,602,212 | 7/1986 | Hiroshima et al. | 324/227 |
| 4,625,165 | 11/1986 | Rothstein | 324/220 |
| 4,739,261 | 4/1988 | Sugiyama et al. | 324/232 |

FOREIGN PATENT DOCUMENTS

| | | |
|---|---|---|
| 56-154657 | 11/1981 | Japan . |
| 252631 | 11/1970 | U.S.S.R. . |
| 673904 | 7/1979 | U.S.S.R. . |

OTHER PUBLICATIONS

"Two-Frequency Eddy Current Instrument for Measuring the Thickness of Zircaloy Cladding on Uranium under Conditions of Varying Lift-Off" by J. M. Prince, L. D. Reid, and D. L. Lessor, Materials Evaluation, 43, Nov. 1985.
"CO-NETIC & NETIC Magnetic Shielding Alloys", Magnetic Shield Division, Perfection Mica Company, 1982.
"Lab Kit for Magnetic Shielding with AC Magnetic Pickup Probe", Magnetic Shield Division, Perfection Mica Company, 1983.

*Primary Examiner*—Reinhard J. Eisenzopf
*Assistant Examiner*—Jack B. Harvey

[57] ABSTRACT

An improved eddy current probe system and method for simultaneously detecting different types of flaws at different depths within a metallic wall, such as a section of Inconel tubing, is disclosed herein. The system comprises a current generator for generating alternating currents of substantially different frequencies, a probe head including first, second and third concentrically arranged coils in separate communication with the current generator, shielding material disposed between the coils for preventing cross talk between each coil and the pulsating magnetic field of the coils adjacent to it, and a detector circuit which may include an inductive bridge for providing an electrical output representative of the impedance changes in the respective coils. In operation, each of the coils conduct currents having substantially different frequencies, the highest frequency being conducted by the smallest-diametered coil and the lowest frequency being conducted by the largest-diametered coil. The different levels of magnetic field penetration provided by the coils as it is helically moved around the inside surface of a section on Inconel tubing not only allows the probe system to detect diverse kinds of flaws such as cracks, pits, or regions of thinning, but also flaws located at different depths throughout the tube wall. In the method of the invention, a computer is used to adjust the frequencies of the alternating currents conducted through the coils during the scanning operation in order to maximize the impedance changes in each coil, thereby maximizing the resolution of the probe system.

28 Claims, 5 Drawing Sheets

MULTIPLE COIL EDDY CURRENT PROBE AND METHOD OF FLAW DETECTION

BACKGROUND OF THE INVENTION

This invention generally relates to an eddy current probe system and method, and is specifically concerned with an improved probe system having a plurality of concentrically-disposed coils for simultaneously detecting different types of flaws or disconinuities at different depths within a wall of, for example, an Inconel ® tube.

Eddy current probes for inspecting the walls of metallic conduits are known in the prior art. Such probes are particularly useful in inspecting the Inconel tubes used as heat exchangers in nuclear steam generators for flaws caused by corrosion or fretting. Generally, these eddy current probes comprise a coil mounted in a probe head that is slidably movable within the interior of the tube being inspected, and electrically connected to a current generator which conducts an alternating current through the coil as it is moved. The current generator is typically capable of generating alternating currents having frequencies of between 10 kHz and 1 MHz. An impedance detecting circuit, which may take the form of an inductive bridge. is also connected across the leads of the coil. In operation, the alternating current conducted through the coil excites it into generating a pulsating magnetic field whose magnitude and polarity changes in accordance with the frequency of the current. When the coil of the probe is positioned in the vicinity of an electrically conductive wall, the changing magnetic flux emanating from the coil induces eddy currents in a portion of the wall. The particular voltage, amperage and direction of the eddy currents produced are dependent in part upon the specific impedance of the portion of the wall that conducts the eddy current. Because the direction of flow of the eddy currents generated by the coil is opposite to the current flowing through the probe coil, the magnetic field created by the eddy currents creates an impedance in the probe coil. The impedance experienced by the eddy currents is in turn dependent upon the resistance these currents encounter as they circulate through the wall. Since flaws in the metal wall (such as cracks, pits, or regions of local thinning) create regions of higher resistances at the flaw locations, eddy current probes may be used to locate flaws by constantly monitoring the impedances of the coils as the probe coils are moved along the walls of the tube. Sharp changes in impedance over localized areas would indicate the existence of cracks or pits or other relatively small-area flaws, whereas gradual changes in impedance over a broad region of the conduit might indicate large-area flaws such as a grain change in the metal, an area of material creep, or a thinned wall region.

Typically, such prior art eddy current probes utilize either a single bobbin type coil whose axis of rotation is parallel with the longitudinal axis of the conduit being inspected (and which is operated in an "absolute" mode), or a pair of bobbin coils having the same radius which are spaced apart from one another (which are operated in a "differential" mode). In either case, the probe head containing either the single or the double coil is moved within the interior of the tube along its longitudinal axis. More recently, "pancake-type" probe coil configurations have come in to use. In such configurations, the axis of rotation of the windings of a relatively flat coil is disposed along the radius of the conduit, and the coil is used to scan the inner wall of the conduit by moving it both radially and longitudinally, thereby imparting a helical motion to the coil. Such pancake-type coils are capable of more accurately locating the precise point where some types of flaws reside in the conduit wall. Both configurations have been successfully used in hostile environments where direct inspection of tubing is impossible, such as the walls of the approximately 40 miles of Inconel tubes used as heat exchangers in nuclear steam generators.

While such probes are capable of performing satisfactory inspections of such heat exchanger tubes, the applicants have noted a number of problems associated with these probes which, up to now, has limited their usefulness. For example, since the depth of penetration of a particular pulsating magnetic field is dependent upon its frequency, it is difficult or impossible for a coil conducting an alternating current of a fixed frequency to simultaneously and reliably resolve flaws at all depths of the conduit wall. Secondly, while a small-diametered coil is best able to accurately pinpoint the location of a particular flaw, such a coil is incapable of transmitting pulsating magnetic fields having frequencies low enough to completely penetrate the conduit walls if the coil diameter is made too small. The applicants have observed that these constraints often necessitate multiple scans of the tube wall with different diametered coils operating at different frequencies if all of the flaws therein are to be accurately and reliably located. However, the multiple scanning of a particular tube wall with different probe coils operating at different current frequencies greatly protracts the time necessary for the testing which in turn results in increased down-time for the steam generator being inspected. As the typical revenue losses associated with such generator down-time often exceeds $100,000.00 a day, the expenses associated with the necessary multiple scans are very substantial Moreover, such multiple scanning also increases the time that the inspecting personnel are exposed to potentially hazardous radiation, which adds even more to the cost of the eddy current testing.

In view of the foregoing, the applicants have concluded that there is a need for an eddy current probe system which is capable of accurately and reliably plotting all types of flaws at all different depths within the walls of a small diametered metallic tube with only a single rapid scan. Ideally, such an eddy current probe system would provide better resolution than any prior art probe system or combination of any such systems. Finally, the eddy current probe system should be extremely versatile, and capable of instantaneously adjusting its pulsating magnetic fields for maximum coupling with the flaw areas detected so as to afford maximum resolution under a broad range of conditions.

SUMMARY OF THE INVENTION

Generally speaking, the invention is an improved eddy current probe for simultaneously detecting different types of flaws at different depths. The improved probe includes a current generator for generating alternating currents of substantially different frequencies, and a plurality of concentrically arranged coils, each of which separately communicates with the current generating means and each of which conducts an alternating current of substantially different frequency for detecting different types of flaws at different depths within the metallic wall. A magnetic shielding material is disposed between the edges of adjacent coils for preventing cross-talk between each coil and the pulsating magnetic fields generated by adjacent coils. The probe system further includes an impedance detector circuit for providing an electrical output representative of the relative impedance of the respective coils. Both the current generator means and impedance detector circuit may be parts of a commercially available eddy current testing device.

Preferably, the highest frequency alternating current is conducted through the coil having the smallest diameter, whereas the lowest frequency alternating current is conducted through the coil having the largest diameter, for two reasons. First, the application of a relatively low frequency alternating current to the largest diameter coil insures that at least one of the pulsating fields emanating from the coils will penetrate far enough into the tube wall and resolve flaws located on the exterior tube surface, such as areas of grain change, creep and wall thinning due to corrosion, fretting or mechanical scratching. Second, the application of a relatively high frequency alternating current to the smallest diameter coil not only allows this coil to detect and to pinpoint the location of small area flaws such as cracks and pits, but also creates a small and well defined reference point that the probe system operator may use to infer the location of all of the other coils in the probe head at all times. The probe head of the preferred embodiment includes three concentrically disposed coils of progressively larger diameter which may conduct frequencies as high as 1.0 MHz and as low as 30 kHz. The inner coil preferably initially conducts an alternating current of approximately 500 kHz, the middle coil a current of approximately 250 kHz, and the outer coil a current of approximately 50 kHz.

Finally, the improved eddy current probe system may include a computer connected to both the impedance detector circuit and the current generator for adjusting and multiplexing the frequencies of the alternating current conducted through the coils of the probe head as the head is moved along a selected portion of the metallic wall and comparing the resulting amounts of coil impedance detected in order to minimize the impedance of each coil and hence to maximize the flaw-detecting resolution of the probe head.

In the method of the invention, the computer receives and stores the value of the impedance of each coil as the probe is helically moved around the interior of the tube wall. When impedance changes are detected, the computer incrementally adjusts the frequencies of these currents either upwardly or downwardly, and compares the values of the impedances of each coil associated with both the old frequency and the new incrementally adjusted frequency. The computer makes subsequent incremental adjustments to the alternating current frequencies based on the resulting comparisons for the purpose of arriving at the minimum impedance values achievable with the coils. When such maximum impedances are obtained, the resolution of the probe head, as a whole, is maximized.

The probe system of the invention obviates the need for multiple scans of the tube wall being inspected. The concentric arrangement of the coils locates flaws and other discontinuities in a faster and more accurate manner than would a colinear or other multiple arrangement of such coils due to the clear reference point provided by the centrally disposed, small diameter coil which preferably transmits a sharply focused, high-frequency pulsating magnetic field. Finally, the near-instantaneous, impedance minimizing adjustments of the frequencies of the alternating currents conducted through the various-diametered coils insures that the resolution of the probe head will be maximized at every point of inspection without any significant sacrifice in scanning time.

BRIEF DESCRIPTION OF THE SEVERAL FIGURES

Figure 1:
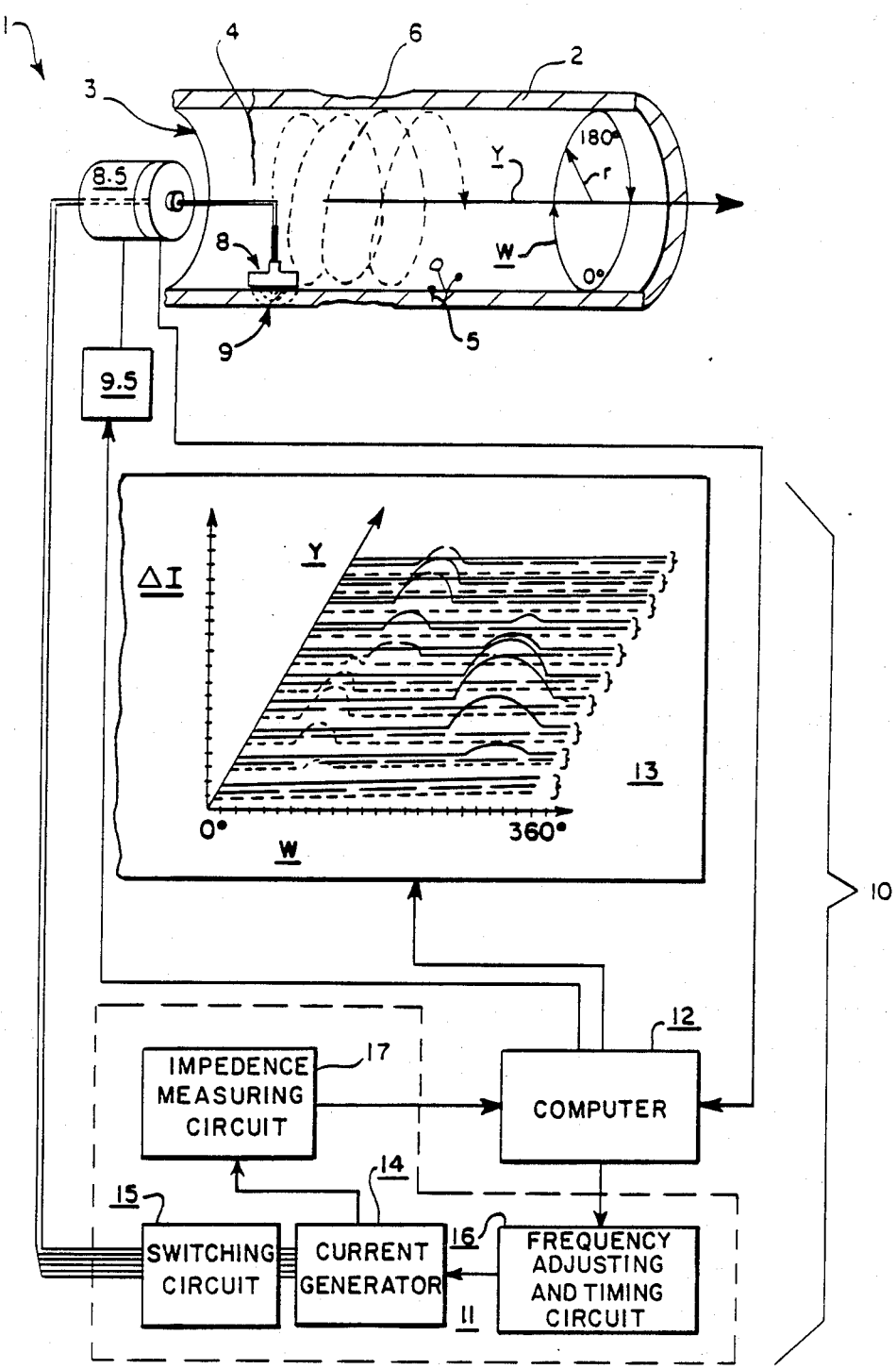
FIG. 1 is a schematic representation of the overall system of the invention, illustrating both the manner in which the probe head scans a tube, the manner in which the probe output is displayed, and the lay-out of the components of the eddy current circuitry that implements the method of the invention.
Figure 4A:
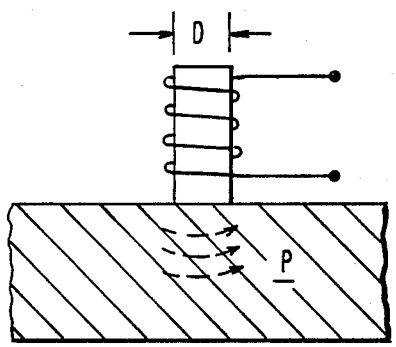
Figure 4B:
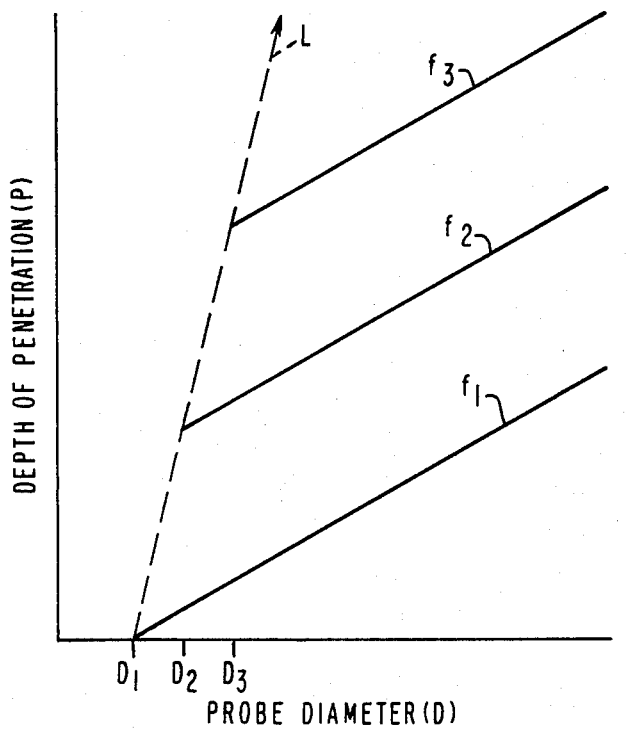
Figure 5A:
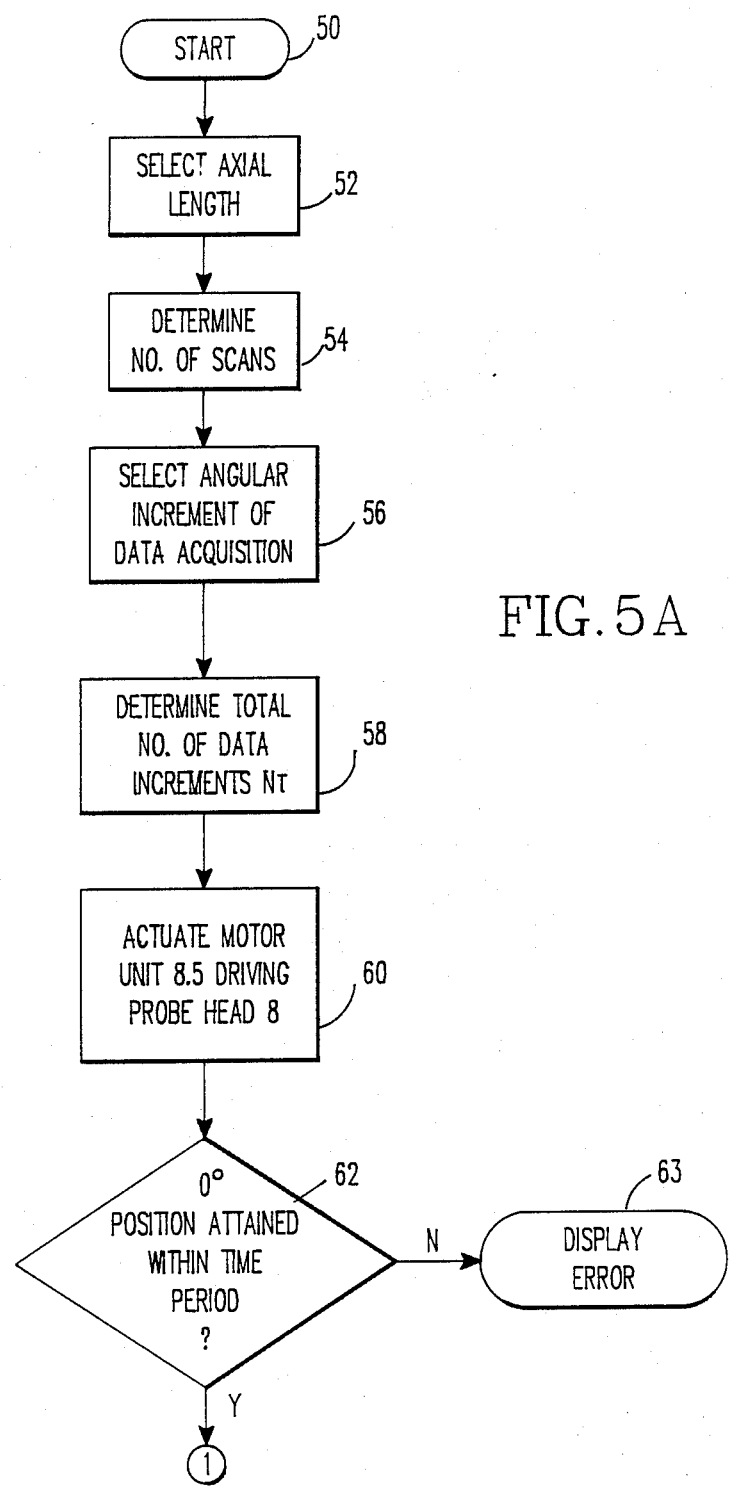
Figure 5B:
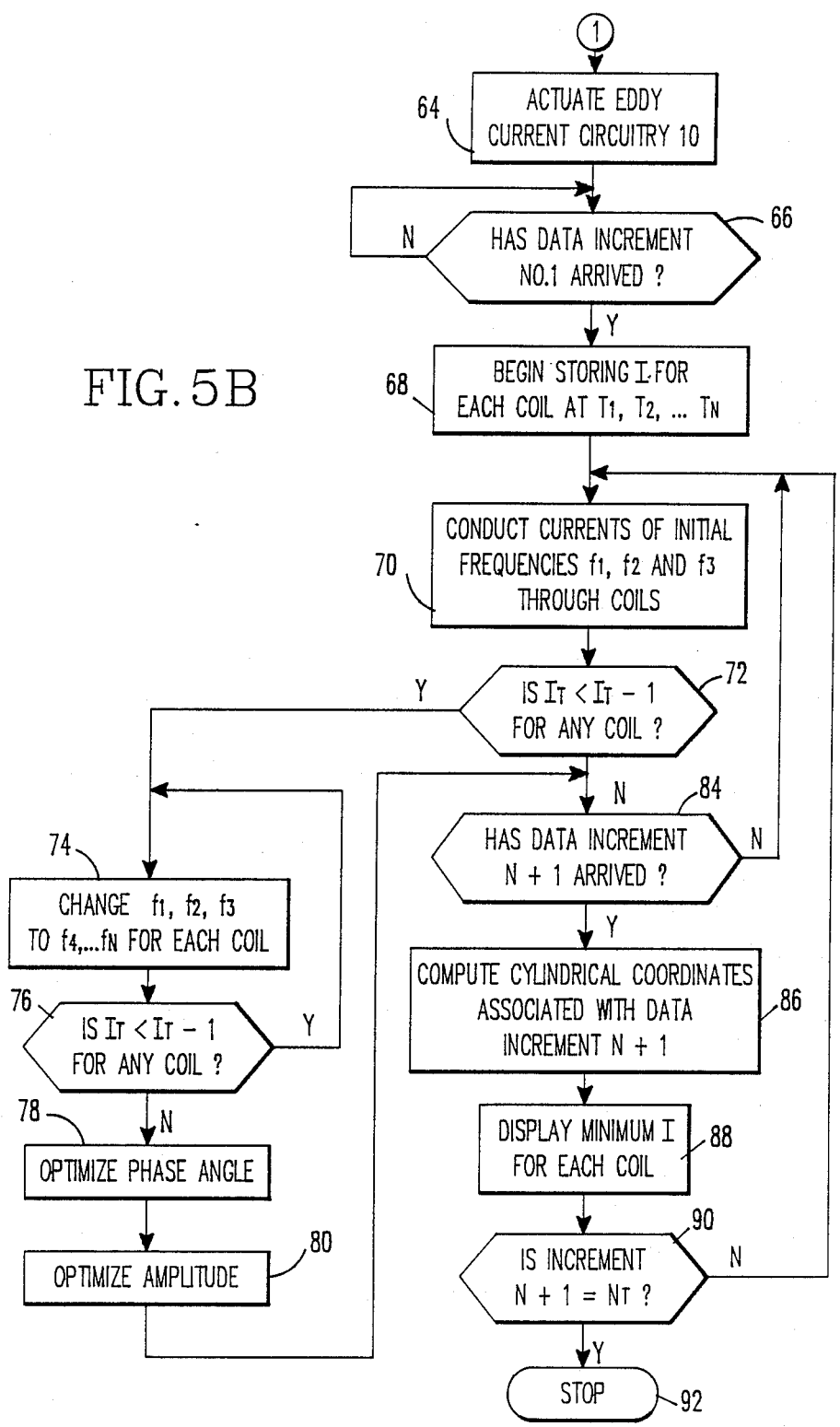

FIGS. 4A and 4B are a schematic diagram of a pancake-type eddy current probe coil, and a graph representing the relationship between the depth of penetration of the pulsating magnetic field emanated by a particular probe coil as a function both of the diameter of the probe, and the frequency of the alternating current applied thereto, and FIGS. 5A and 5B together form a flow chart illustrating the preferred method of the invention as implemented by the circuitry illustrated in FIG. 1.

DETAILED DESCRIPTION OF THE PREFERRED EMBODIMENT

General Description of the Structure and Method of the Invention

With reference now to FIG. 1, wherein like numbers designate like components throughout all the several figures, the eddy current probe system 1 of the invention is particularly well adapted for inspecting the walls 2 of an Inconel tube 3 of the type used in nuclear steam generators for different types of flaws at different depths within the walls 3, such as cracks 4 (both axially and radially aligned), pits 5, and broader sections 6 of the tube wall which have been subjected to creep or grain change, or thinned by corrosion, fretting or mechanical abrasion. The probe system 1 includes a probe head 8 which emanates a magnetic field 9 generated by a multiplicity of concentrically-arranged coils, each of which conducts a different frequency alternating current. The probe head 8 is mechanically mounted in a probe body (not shown) that is moved along a helical path by a drive unit 8.5 that includes an electric drive motor coupled to an optical encoder. The drive unit 8.5 is selectively actuated by a switching circuit 9.5 that is in turn connected to a power source (not shown).

The probe head 8 is electrically connected via a cable to eddy current circuitry generally designated at 10. This eddy current circuitry 10 includes a computer-compatible frequency multiplexer 11 which, in the preferred embodiment, is a model MIZ 18 manufactured by Zetec, Inc., located in Isaquah, Washington. The frequency multiplexer 11 is connected to a computer 12 which is programmed to adjust the frequencies of the currents conducted through the coils of the probe head 8 to optimize resolution whenever an impedance change indicative of a flaw or other discontinuity is detected. In the preferred embodiment, the computer 12 is preferably a Model HP 9836 and an IEEE 488 interface circuit manufactured by Hewlett-Packard located in Palo Alto, California, modified by a Zetec DDA-4 processing package.

The output of the computer 12 is connected to a cathode ray tube (CRT) 13 which displays, through selected computer graphics, the impedance changes experienced by the coils within the probe head 8 as they are helically moved around the inner surface of the wall 2 of the Inconel tube 3. The frequency multiplexer 11 includes a current generator 14 for generating a multiplicity of alternating currents. The leads of the concentrically arranged coils within the probe head 8 are connected to the current generator 14 by way of a switching circuit 15. This switching circuit 15 acts to selectively conduct the same current through one or more of the concentrically arranged coils in the probe head 8 when the overall resolution of the system 1 would be enhanced by such an interconnection The current generator 14 is connected to and controlled by a frequency adjusting and timing circuit 16. The circuit 16 is capable of not only changing the frequency of the currents conducted through each of the concentrically arranged coils of the probe head 8, but also of multiplexing a sequence of different-frequency currents through each of the coils. Finally, the frequency multiplexer 11 includes an impedance measuring circuit 17 which may be an inductive bridge connected to the current generator 14 for measuring changes in impedance experienced by the concentrically arranged coils in the probe head 8 as they are helically moved along the tube 3.

In operation, the probe head 8 is mounted within a probe body such as the Delrin ® probe carrier of the combined ultrasonic and eddy current inspection probe described and claimed in co-pending U.S. patent application Ser. No. 079,860, filed July 30, 1987, by Thomas Arzenti and assigned to the Westinghouse Electric Corporation, the entire specification of which is incorporated herein by reference. The probe carrier of the aforementioned probe helically moves the probe head 8 in wiping engagement with the inner surface of the wall 2 of an Inconel tube 3 to scan the same. As is indicated in FIG. 1, such helical motion includes an axial component along the longitudinal axis Y of the tube 3, as well as an angular component w along the radius r of the tube 3. As will be described in more detail hereinafter, as the probe head 8 is scanningly moved throughout the inner surface of the tube wall 2, different frequencies of alternating current are conducted through different probe coils so as to generate a plurality of different shaped pulsating magnetic fields. At least one of these coils generates a field that penetrates completely through the wall 2 of the tube 3 so that exterior surface flaws such as the thinned portion 6 of the tube may be detected. At least one of the coils generates a magnetic field which interacts substantially with the inner surface of the wall 2 of the tube 3 so that interior surface flaws such as pit 5 which exist predominantly in the interior portion of the wall 2 may be detected. Finally, at least one of the coils in the probe head 8 generates a pulsating magnetic field whose lines of flux interact principally with the interior portion of the wall 2 in order to resolve flaws such as the crack 4 which extends completely through the wall 2 of the tube 3.

The results of the scan may be displayed on the CRT tube 13 by way of computer graphics wherein the vertical axis designates the impedance changes experienced by each of the coils, the perspective axis represents the longitudinal axis Y of the tube 3 and the horizontal axis represents the angular location of the probe head 8 with respect to the radius of the tube 3. Preferably, each one of the ten scans illustrated on the CRT screen 13 includes a different-colored output for each of the coils in the probe head 8. In the preferred embodiment of the invention, three coils are used in the probe head 8, although many more of such coils may be used if desired. In the graph displayed on CRT screen 13, the output of the small-frequency coil is illustrated by a small-dashed line, while the output of the medium and low frequency coils are represented by large-dashed and solid lines, respectively. In the preferred embodiment, the small, medium and large diametered coils are initially operated at 500, 250 and 50 kHz respectively, and are adjusted to maximize the resolution of the probe system 1 when an impedance change indicative of a flaw is detected.

Specific Description of the Structure and Method of the Invention

Figure 2:
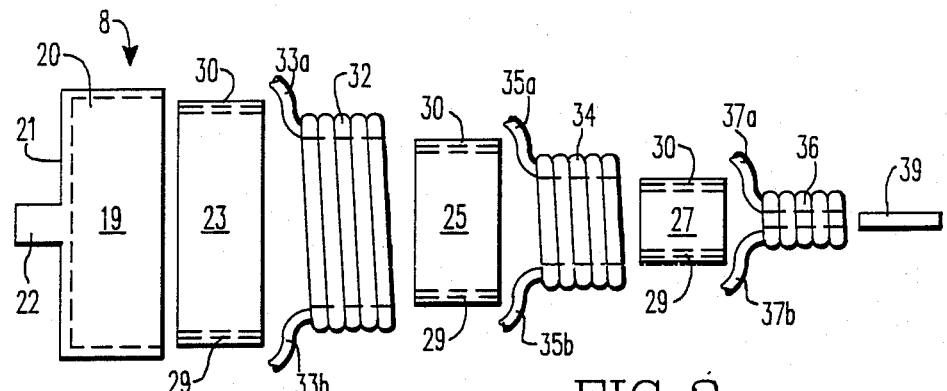
FIG. 2 is an exploded, side view of the probe head of the invention.
Figure 3A:
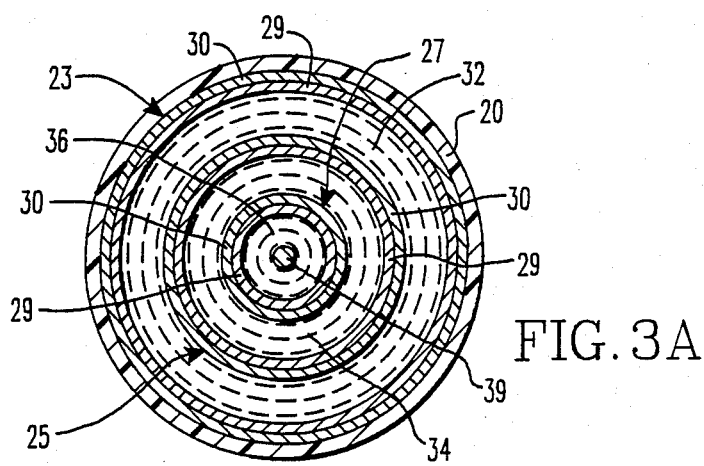
FIG. 3A is a plan view of the probe head illustrated in FIG. 2 with the coils shown in phantom.
Figure 3B:
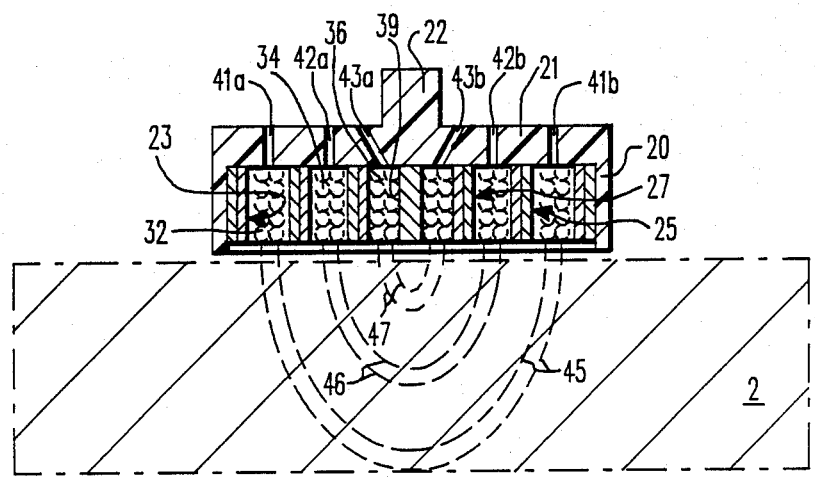
FIG. 3B is a cross-sectional side view of the probe head illustrated in FIG. 3A.

With reference now to FIGS. 2 3A and 3B, the exterior of the probe head 8 is formed by a casing 19 preferably fabricated from a plastic material such as Delrin. The casing 19 includes a ring-shaped side wall 20 for retaining the coils and the probe head 8, as well as a circular back plate 21 having a centrally disposed mounting lug 22 projecting therefrom. In the preferred embodiment, the ring-shaped side wall 20, the circular back plate 21 and mounting lug 22 are all integrally formed. The interior of the probe head 8 includes outer, middle and inner shield walls 23, 25 and 27, as well outer, middle and inner probe coils 32, 34, 36. Each of the shield walls 23, 25 and 27 is formed from a ring 29 of material that is very high in magnetic permeability which is closely circumscribed by a ring 30 of material which is somewhat lower in magnetic permeability but which has higher saturation characteristics than the ring 29 that it circumscribes. In the preferred embodiment, the inner ring 29 of each shield is formed from Netic* foil, while the outer ring 30 of each shield is formed from Co-Netic* foil. The ring-shaped shield walls 23, 25 and 27 insulate each of the coils 32, 34 and 36 from the pulsating magnetic fields created by the coils adjacent thereto by providing a low reluctance path that diverts potentially interfering magnetic fields from the coil surrounded thereby. Such shielding in turn prevents inter coil cross-talk during the operation of the probe system 1. As is evident in FIG. 2, each of the coils 32, 34 and 36 includes a pair of leads 33a, 33b, 35a, 35b and 37a, 37b which is ultimately connected to the frequency multiplexer 11 by way of a cable as indicated in FIG. 1. Also, a ferrite focusing core 39 is centrally disposed within the inner coil 36 in order to both focus and intensify the pulsating magnetic field generated thereby, thereby advantageously creating a reference point for inferring the location of the surrounding coils 32 and 34. While a total of three coils are shown in the preferred embodiment, a greater number of coils could be used if desired.

*CO-netic and Netic are registered U.S. trademarks owned by the Magnetic Shield Division of Perfection Mica Co. of Beusenville, Ill.

In the preferred embodiment, both the outer, middle and inner probe coils 32, 34 and 36 are formed from about thirty windings of copper wire. As the outer diameter of the probe head 8 is only about 0.1875 inches, these windings are formed from very thin wire. In the alternative, the coil windings may also be formed from state-of-the-art printed circuit board techniques. Probe head coils formed by way of this latter method are advantageously flatter than coils formed by bobbin-like windings of copper wire. Such extreme flatness might have the affect of increasing the overall resolution of the probe head 8 since the fields generated by the coils 32, 34 and 36 would not significantly project out of the back side of the probe head 8, where they might have an opportunity to interact with a metallic body which is not the particular portion of the conduit wall 2 being inspected. In both embodiments, the front face of the probe head 8 is coated with a thin layer of Delrin or some other self-lubricating plastic material both to protect the delicate coil windings, and to minimize friction as the probe head 8 helically rides along the inner surface of the tube wall 2 being inspected.

With reference now to FIGS. 3A and 3B, the casing 19 of the probe head 8 further includes three pairs of lead bores 41a, 41b, 42a, 42b, and 43a, 43b for conducting the lead wires 33a, 33b, 35a, 35b, and 37a, 37b of the coils 32, 34 and 36 respectively. As is indicated in FIG. 1, these lead wires are ultimately connected to the switching circuit 15 of the frequency multiplexer 11 by way of a cable which extends through the drive unit 8.5 by way of appropriate slip-ring connectors (not shown).

The general operation of the probe head 8 may best be understood with reference to FIGS. 3B, 4A and 4B. At the beginning of each data increment, the frequencies of the currents conducted through the coils 32, 34 and 36 are selected so that the field 45 emanated by the largest-diametered coil 32 will penetrate completely through the wall 2 of the Inconel tube 3 being inspected, while the field 47 emanated by the smallest-diametered coil 36 will only shallowly penetrate into the inner surface of the wall 2. The field 46 emanated by the middle-diametered coil 34 interacts primarily with the interior of the wall 2 of the tube 3. Such a field shape insures that no significant discontinuity at any point along the wall thickness will be overlooked by the probe system 1.

While it would be possible to operate the largest diametered coil 32 at the highest frequency, and the smallest diametered coil 36 at the lowest frequency, such a mode of operation is normally not preferred by virtue of the limitations illustrated in the graph of FIG. 4B. This graph demonstrates that the depth of penetration of the pulsating magnetic field emanating from a particular coil is dependent not only upon the frequency of the current conducted through the coil, but also upon the diameter of the coil. This graph also illustrates that, in order to achieve a particular depth of penetration P, the coil diameter D must be of a certain minimal size before any effective penetration can take place, no matter how low the frequency of the current conducted thereby. Hence, the diameter of the smallest-diametered coil 36 may well be below the minimum size diameter necessary to project a pulsating magnetic field completely through the wall 2 of an Inconel tube 3. Of course, the diameter of the smallest diametered coil 36 could be made large enough to project a field through the wall. But if this were done, the resolution ability of the probe head 8 might be seriously diminished, since the resulting large coils would not be capable of accurately locating the borders of small area flaws. For all these reasons, the smallest-diametered coil 36 is generally operated at the highest frequency, while the largest-diametered coil 32 is operated at the lowest frequencies.

FIGS. 5A and 5B form a flow chart which specifically represents the method of the invention as implemented by the computer 12. After the probe body (not shown) carrying the probe head 8 has been slidably inserted into a particular heat exchanger tube 3 so that the probe head 8 is adjacent to the region of the tube 3 that the operator wishes to inspect, the operator first selects the precise axial length of the tube 3 that he wishes to scan as indicated by box 52. Next. the computer 12 converts this axial length into numbers of scans, as is indicated by box 54. This is a simple operation, which is determined on the basis of the pitch of the thread of the screw (not shown) used to impart helical motion to the probe body.

After the computer 12 has determined the number of scans corresponding to the selected axial length of the tube 3 to be inspected, the system operator next selects and angular increment of data acquisition, as is indicated by box 56. If the operator desires a relatively quick, coarse resolution scan of the tube 3, this angular increment may be as high as 15 degrees. If, on the other hand, he wishes to have a relatively quick, fine resolution scan made of the axial length being inspected, this angular increment may be as low as 1 degree. Normally, to provide for a uniform resolution throughout the entire 360 degrees of the scan, the angular increment chosen will be a number of degrees which is evenly divisible into 360 degrees.

In the next step of the method, the computer 12 determines the total number of data increments Nt to be taken by determining the number of angular increments in each scan, and multiplying times the number of scans computed in step 54. After this has been accomplished, the drive unit 8.5 that moves the probe head 8 is actuated as is indicated by step 60. This is accomplished by the computer 12 actuating the power switching circuit 9.5, which connects the electric motor of the drive unit 8.5 to a source of electrical power (not shown). Immediately after the motor has been actuated, the output of the optical encoder coupled to the drive unit motor is fed into the input of the computer 12.

Once the computer 12 begins to receive an output from the optical encoder of the drive unit 8.5, it inquires whether or not the encoder rotates past a zero degree position within a selected time period, as is indicated by question block 62. If the computer 12 does not receive such a confirmation signal, it displays an error condition, as is indicated by block 63, which informs the operator of the probe system 1 that the motor and encoding unit 8.5 is not properly rotating the probe head 8. If, on the other hand, it receives a signal that indicates that the encoder of the motor and encoder unit 8.5 has swept past a zero degree position within a selected time period, it proceeds to block 64, and actuates the eddy current circuitry 10.

After the eddy current circuitry 10 has been actuated, the computer 12 proceeds to question block 66, and inquires whether or not the drive unit 8.5 has moved the probe head 8 to the beginning of the first data increment. As the data increments are only about 6 mils apart when the probe head 8 is used to inspect a ⅜ inch diameter heat exchanger tube at 1-degree increments, the amount of time necessary for the computer 12 to answer the inquiry in question block 66 in the affirmative is normally only a small fraction of a second. As soon as the computer 12 detects that the beginning of the first data increment has arrived, it immediately begins storing the impedances associated with each coil 32, 34 and 36 as indicated in box 68. At substantially the same time, the computer 12 instructs the frequency multiplexer 11 to conduct current of initial frequencies F1, F2 and F3 through the coils 32, 34 and 36. In the case of an Inconel heat exchanger tube having a wall thickness of approximately 0.05 in., F1, F2 and F3 will correspond to 50 kHz, 250 kHz, and 500 kHz, respectively when the outer diameter of the coil 32 is approximately 0.1875 inches and the outer diameter of the inner coil 36 is approximately 0.0625 inches. The applicants have observed that the conduction of currents of such frequencies into coils of such diameters result in magnetic fields that interact with tube walls of such thicknesses in much the fashion shown in FIG. 3B, wherein the field lines 45 emanated by the largest-diametered coil 32 penetrate completely through the wall 2 of the tube 3, and the field lines 46 and 47 of the mid-diametered and smallest-diametered coils 34 and 36 penetrate the interior and the inner surface of the wall 2 as illustrated.

Immediately at the commencement of the first data increment, the computer proceeds to question block 72, and inquires whether or not the eddy current circuitry wall 2) the computer 12 implements the step indicated in block 74, and immediately begins changing the frequencies of the currents conducted through the coils 32, 34 and 36 in order to optimize resolution. Every time a current of a new frequency is conducted through one of the coils, the computer proceeds to question block 76 and inquires whether or not the impedance experienced by any of the coils 32, 34 and 36 has decreased as a result of the changes in frequency of the current conducted therethrough. If the answer to this question is affirmative, then the computer 12 returns to the step indicated in block 74, and continues to change the frequency of the current on a millisecond to millisecond basis. Of course, the practical effect of the steps indicated in blocks 74 and 76 is for the computer 12 to search out and find the frequency of the currents in the coils 32, 34, and 36 which minimize the coil impedance, and thereby maximize the resolution of the flaw in the tube wall 2.

Once these optimum frequencies have been found, the answer to the inquiry in question block 76 will become negative, and the computer 12 will proceed to further optimize resolution by optimizing the phase angle of the alternating currents flowing through the coils 32, 34 and 36, and then optimizing the amplitudes of the resulting signals as is indicated in blocks 78 and 80.

Immediately after all of the optimization steps 74 through 80 have been completed, the computer will proceed to question block 84, and ask whether or not the next data increment N+1 has arrived. If the answer is negative, then the computer 12 will re-execute the step indicated in block 70, and again conduct the initially chosen current frequencies through the various coils, which again will likely result in a near repeat of the steps indicated in block 72 through 80. However, when the answer to this inquiry is a firmative, the computer computes the cylindrical coordinates associated with the data increment step N+1 as is indicated in block 86. It will then immediately display the minimum impedance value associated with each of the coils 32, 34 and 36 within the increment as is indicated in block 88. Lowered impedance values will have the effect of generating hills in the graphic display on the CRT tube 13, such as illustrated in scans 2 through 5 in FIG. 1.

Next, as is indicated by question block 90, the computer 12 will inquire whether or not the data increment just completed completes the total number of data increments Nt. If the answer to this question is negative, the computer 12 recommences steps 70 through 90. When, however, the answer to this inquiry is affirmative, the computer 12 stops the operation of the probe system 1, as is indicated by block 92.

Of course, if the computer 12 detects no discontinuities in the tube wall 2 in a particular data increment, it answers the question in question block 72 in the negative, and continues to conduct currents through the coils 32, 34 and 36 at the initially chosen frequencies until the end of that data increment. Following this, the computer 12 displays the impedance values at the cylindrical coordinates associated with the no-flaw increment. As the impedance values remain unchanged throughout such a data increment, the resulting display is a straight segment. If no impedance changes are detected throughout a complete scan, the resulting display is a straight line for the entire scan (such as scan no. 1 in FIG. 1).

While the flowchart of the method of the invention has been described only in terms of changing the frequencies of the currents conducted through the coils 32, 34 and 36 in order to achieve the desired result of maximum resolution, the general program may be embellished with one or more subroutines which would enhance the resolution of the probe head 8 even more. For example, when the smallest-diametered coil 36 detects a flaw on the inner surface of the tube wall 2, the concentrically disposed middle and outer coils 34 and 36 could be operated at the same high frequency for a very small fraction of a second. If one or more of these larger diametered coils simultaneously interacted with this inner surface flaw, the resulting information could help determine the area of the flaw since the area of the coils in the probe head 8 is known. Still another subroutine that might be added to the general program is the operation of two of the three coils in a differential mode, in contrast to the operation of all three coils in an absolute mode.

While the aforementioned method of the invention has been described with respect to the use of three coils, it is also adaptable for use with a probe head 8 having more than three coils. If more than three coils are used, a larger span of initially chosen frequencies are preferably used, which would have the effect of increasing the overall resolution of the system 1 even more.

We claim:

1. An improved eddy current probe system for simultaneously detecting different types of flaws at different depths within a metallic wall, comprising:
   a. current means for generating alternating current of substantially different frequencies including a frequency adjuster and timing means;
   b. a probe head including first and second coils in separate communication with said alternating currents of substantially different frequencies for detecting different types of flaws at different depths within said metallic wall, wherein the windings of one coil surround the windings of the other coil;
   c. shielding means for preventing cross talk between said coils;
   d. detector means for providing an electrical output representative of the relative impedance of the respective coils, and e. a computing means connected to said detector means and said current generating means for receiving and storing the value of the impedance of each coil as the probe head is moved across a portion of said metallic wall, and for transmitting control signals to said frequency adjuster and timing means which cause the current generating means to adjust the frequency of the alternating currents received by the coil so that impedance changes in the coils and hence the flaw-detecting resolution of each is maximized.

2. An improved eddy current probe system as defined in claim 1, wherein the windings of said coils are substantially circular, and wherein the windings of the first coil circumscribe the windings of the second coil.

3. An improved eddy current probe system as defined in claim 2, wherein the first coil is substantially concentrically disposed around the second coil.

4. An improved eddy current probe system as defined in claim 1, wherein the current means applies a lower frequency alternating current to the surrounding coil, and a substantially higher frequency alternating current to the surrounded coil.

5. An improved eddy current probe system as defined in claim 4, wherein the frequency of the alternating current applied to the surrounding coil is low enough to detect flaws occurring relatively deep within said metallic wall, and the frequency of the alternating current applied to the surrounded coil is high enough to detect flaws on the surface of said metallic wall.

6. An improved eddy current probe system as defined in claim 4, wherein the frequency of the current applied to the surrounding coil is low enough to detect flaws covering a relatively wide area of said metallic wall, and the frequency of the alternating current applied to the surrounded coil is high enough to detect flaws covering a relatively narrow areas of said metallic wall.

7. An improved eddy current probe system as defined in claim 1, wherein the current means applies an alternating current having a frequency of at least 30 Khz to the surrounding coil, and an alternating current having a frequency no greater than 1.0 MHz to the surrounded coil.

8. An improved eddy current probe system as defined in claim 1, wherein the windings of said first coil surround the windings of the second coil, and further including a third coil whose windings surround the windings of the first coil.

9. An improved eddy current probe system as defined in claim 8, wherein the frequency of the alternating current applied to the second, first and third coils is relatively higher for each coil, respectively.

10. An improved eddy current probe system as defined in claim 9, wherein the frequency of the alternating current applied to the second, first and third coils is between about 300 and 700 kHz for said second coil, 50 and 450 kHz for said first coil, and 20 and 100 kHz for said third coil.

11. An improved eddy current probe system for simultaneously detecting different types of flaws at different depths within a metallic wall, comprising:
  a. current means for generating alternating currents at a plurality of different frequencies, including a frequency adjuster and timing means;
  b. a probe head including a plurality of different coils having a different diameters arranged substantially concentrically, each of which is separately connected to said current means for receiving one of said currents of different frequencies;
  c. shielding means disposed between the edges of adjacent coils for preventing cross talk between the fluctuating magnetic fields generated by each coil and the coils adjacent to each such field;
  d. detector means for providing an electrical output representative of impedance changes in the respective coils, and
  e. a computing means connected to said detector means and said current generating means for receiving and storing the value of the impedance of each coil as the probe head is moved across a portion of said metallic wall, and for transmitting control signals to said frequency adjuster and timing means which cause the current generating means to adjust the frequency of the alternating currents received by the coils so that impedance changes in the coils and hence the flaw-detecting resolution of each is maximized 12. An improved eddy current probe system as defined in claim 11, wherein said shielding means is a plurality of ring-shaped walls of netic-conetic material disposed between the edges of different coils.

13. An improved eddy current probe system as defined in claim 11, further including a ferrite core means disposed within the smallest-diametered coil for concentrating the magnetic flux generated thereby.

14. An improved eddy current probe system as defined in claim 11, further including a switching means 15 connected to said current means for connecting one or more of said plurality of coils in series with one another, so that said serially connected coils may conduct the same alternating current and thereby act as a single coil probe of increased diameter.

15. An improved eddy current probe system as defined in claim 11, wherein the current means applies a progressively higher frequency alternating current to coils of smaller diameter.

16. An improved eddy current probe system as defined in claim 11, wherein said current means conducts a current of between about 300 and 700 Khz to a first coil, 150 to 350 kHz to a second coil that circumscribes the first, and 30 to 70 kHz to a third coil that circumscribes the second.

17. An improved eddy current probe system as defined in claim 16, wherein said current means conducts a current of about 500 kHz to a first coil, 250 kHz to a second coil that surrounds the first, and 50 kHz to a third coil that surrounds the second.

18. An improved eddy current probe system as defined in claim 11, wherein each coil includes a front face confrontable against said metallic wall for transmitting a pulsating magnetic field therefrom that is covered by a self-lubricating plastic material.

19. An improved eddy current probe system particularly adapted to be helically moved in sliding engagement against the inner wall of a metallic conduit for simultaneously detecting both large and small area flaws located at different depths within the conduit walls, comprising:
  a. current generating means for generating alternating currents of different frequencies, and for changing the frequencies of any one of said currents in response to a frequency control signal;
  b. a probe head including a plurality of different coils having different diameters arranged concentrically, each of which is separately connected to said current generating means for receiving and conducting one of said alternating currents, wherein each of said coils includes a front face confrontable against said wall of said conduit for transmitting a pulsating magnetic field therefrom into said wall, and a rear face and wherein the smallest-diametered coil is provided with the highest frequency alternating current by the current generating means to provide a reference point for the system operator;

c. shielding means for minimizing cross talk between said coils and said fields including ring-shaped walls of netic-conetic material disposed between the edges of adjacent coils;

d. detector means for providing an electrical output representative of the relative impedance of the respective coils, and e. computing means connected to said detector means and said current generating means for receiving and storing the value of the impedance of each coil as the probe head is moved in sliding engagement against the inner wall of said metallic conduit, and for transmitting frequency control signals to a frequency adjuster and timing means connected to the current generating means which cause it to adjust the frequency of the alternating currents received by the coils so that the impedance changes detected by the coils and hence the flaw-detecting resolution of each is maximized.

20. An improved eddy current probe system as defined in claim 19, wherein said current generating means conducts a current of between abut 300 and 700 kHz to a first coil, 150 to 350 kHz to a second coil that circumscribes the first, and 30 to 70 kHz to a third coil that circumscribes the second.

21. An improved eddy current probe system as defined in claim 19, wherein said current means conducts a current of about 500 kHz to a first coil, 250 kHz to a second coil that surrounds the first, and 50 kHz to a third coil that surrounds the second.

22. An improved eddy current probe system as defined in claim 19, further including a ferrite core means disposed within the smallest-diametered coil for concentrating the magnetic flux generated thereby.

23. An improved eddy current probe system as defined in claim 19, further including a switching means connected to said current means for connecting one or more of said plurality of coils in series with one another, so that said serially connected coils may conduct the same alternating current and thereby act as a single coil probe of increased diameter.

24. A method for simultaneously detecting different types of flaws in a metallic wall by an improved eddy current probe system that includes a current generating means for generating alternating currents of different frequencies, and a probe head having a plurality of different coils having different diameters arranged concentrically with respect to each other, each of which is separately connected to said current generating means, comprising the steps of:

a. conducting alternating currents of different frequencies through said coils while moving said probe head across a portion of said metallic wall, wherein the frequency of the current conducted through one coil is high enough to detect flaws on the surface of the wall confronting the probe head, and the frequency of the current conducted through another coil is low enough to detect flaws in said wall beyond said confronting wall surface;

b. monitoring the impedance of the coils as the probe head is moved, and c. adjusting the frequencies of the alternating currents conducted through each of the coils to maximize the impedance change in each of the coils.

25. A method for simultaneously detecting different types of flaws in a metallic wall by an improved eddy current probe system as defined in claim 24, wherein the highest frequency current is conducted through the smallest-diametered coil, and the lowest frequency current is conducted through the largest-diametered coil.

26. A method for simultaneously detecting different types of flaws in a metallic wall by an improved eddy current probe system as defined in claim 24, wherein the metallic wall is the internal wall of a metallic conduit, and wherein the concentric coils of said probe head are engaged against and helically moved within said internal wall of said conduit while said current frequencies are adjusted.

27. A method for simultaneously detecting different types of flaws in a metallic wall by an improved eddy current probe system as defined in claim 24, further including the steps of storing the values of the coil impedances for each coil as said probe head is moved over a selected portion of said wall, incrementally changing the frequencies of the alternating currents conducted to the coils, and storing the values of the coil impedances for each coil as said probe head is moved over said selected portion a second time.

28. A method for simultaneously detecting different types of flaws in a metallic wall by an improved eddy current probe system as defined in claim 27, further including the step of comparing the impedance values associated with the first and second probe head movements, and further incrementally changing the values of the alternating currents conducted to the coils in a manner that the impedance change in the coil is maximized.

* * * * *